(12) United States Patent
Borromeo et al.

(10) Patent No.: US 9,796,689 B2
(45) Date of Patent: Oct. 24, 2017

(54) PROCESS FOR PREPARATION OF 4-(1-(4-(PERFLUOROETHOXY)PHENYL)-1H-1,2,4-TRIAZOL-3-YL)BENZOYL AZIDE

(71) Applicant: Dow AgroSciences LLC, Indianapolis, IN (US)

(72) Inventors: Peter Borromeo, Fishers, IN (US); Carl DeAmicis, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/795,319

(22) Filed: Jul. 9, 2015

(65) Prior Publication Data

US 2016/0009665 A1   Jan. 14, 2016

Related U.S. Application Data

(60) Provisional application No. 62/023,225, filed on Jul. 11, 2014.

(51) Int. Cl.
   *C07D 249/08*   (2006.01)
(52) U.S. Cl.
   CPC .................. *C07D 249/08* (2013.01)

(58) Field of Classification Search
   CPC .................................................. C07D 249/08
   See application file for complete search history.

(56) References Cited

U.S. PATENT DOCUMENTS

| | | | |
|---|---|---|---|
| 2009/0209476 A1* | 8/2009 | Crouse et al. | 514/25 |
| 2012/0122805 A1* | 5/2012 | Crouse et al. | 514/23 |
| 2012/0190543 A1* | 7/2012 | Lambert et al. | 504/100 |
| 2014/0135364 A1* | 5/2014 | Lambert et al. | 514/340 |
| 2015/0080326 A1* | 3/2015 | Crouse et al. | 514/25 |

OTHER PUBLICATIONS

Kaiser, Organic Syntheses Coll., 1988, vol. 6, p. 910.*
Starks, Phase-Transfer Catalysis, 1994, p. 339-382.*

* cited by examiner

*Primary Examiner* — Rebecca Anderson
*Assistant Examiner* — Karen Cheng
(74) *Attorney, Agent, or Firm* — Yung H. Lee

(57) ABSTRACT

By either forming a triaryl acid halide or a triaryl mixed anhydride and subsequently treating with aqueous sodium azide, triaryl acyl azides are prepared in high yield using inexpensive reagents in a process in which by-products are easily removed from the triaryl acyl azide.

4 Claims, No Drawings

PROCESS FOR PREPARATION OF 4-(1-(4-(PERFLUOROETHOXY)PHENYL)-1H-1,2,4-TRIAZOL-3-YL)BENZOYL AZIDE

CROSS REFERENCE TO RELATED APPLICATIONS

This application claims the benefit of, and priority from, U.S. Provisional Patent Application Ser. No. 62/023,225 filed 11 Jul. 2014, the entire disclosure of which is hereby expressly incorporated by reference.

BACKGROUND OF THE INVENTION

The present invention concerns an improved process for preparation of 4-(1-(4-(perfluoroethoxy) phenyl)-1H-1,2,4-triazol-3-yl)benzoyl azide.

U.S. Pat. No. 8,178,658 describes, inter alia, certain triaryl rhamnose carbamates and their use as insecticides. One of the methods used to prepare such triaryl compounds is by way of a the following 2 step process

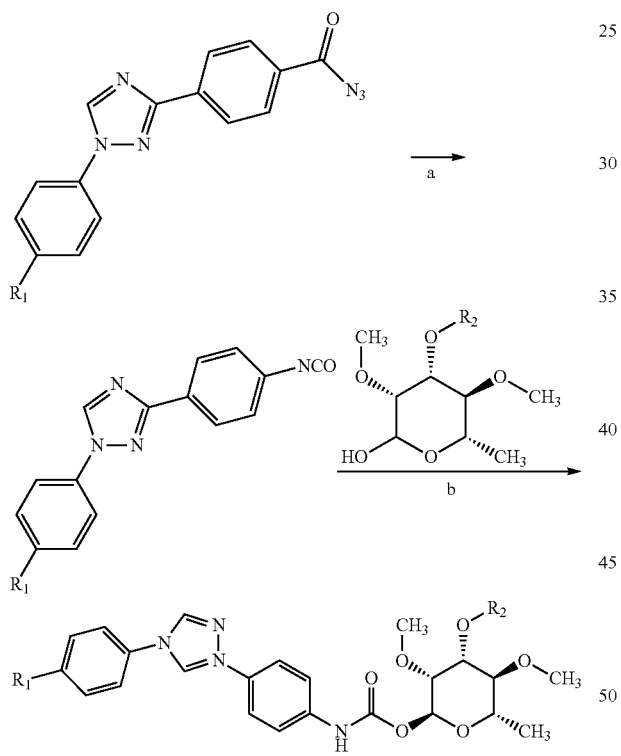

wherein
$R_1$ represents $(C_1-C_6)$ haloalkyl or $(C_1-C_6)$ haloalkoxy, and
$R_2$ represents $(C_1-C_6)$ alkyl, $(C_2-C_6)$ alkenyl, or $(C_2-C_6)$ alkynyl,
in which a triaryl acyl azide is converted to an isocyanate followed by reaction with a tetrahydropyran-2-ol and a strong base to give the triaryl rhamnose carbamate pesticide.

U.S. Pat. No. 8,178,658 describes the preparation of 4-(1-(4-(perfluoroethoxy)phenyl)-1H-1,2,4-triazol-3-yl) benzoyl azide from 4-(1-(4-(perfluoroethoxy)phenyl)-1H-1,2,4-triazol-3-yl) benzoic acid and the azide transfer agent diphenylphosphorylazide.

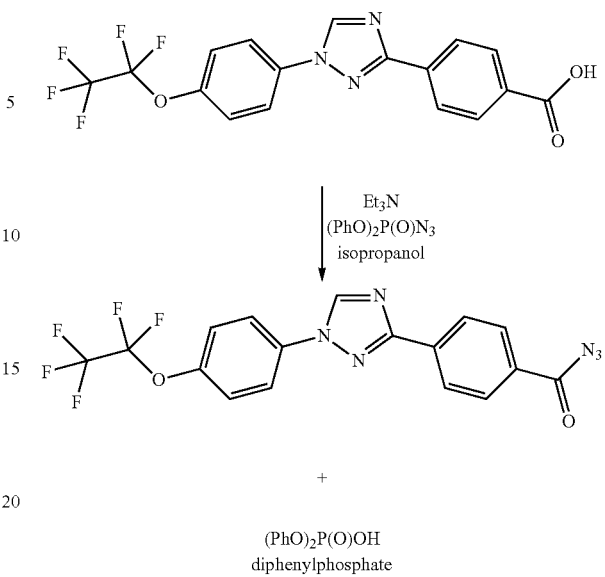

However, diphenylphosphorylazide is a very expensive reagent and is only available in research quantities. Additionally, diphenylphosphorylazide gives yields of the desired acyl azide in the range of 60-80% and the by-product diphenylphosphate is not water soluble and is difficult to remove from acyl azide. Consequently the acyl azide is usually contaminated with 5-10% of the diphenylphosphate. It would also be desirable to prepare 4-(1-(4-(perfluoroethoxy) phenyl)-1H-1,2,4-triazol-3-yl)benzoyl azide from 4-(1-(4-(perfluoroethoxy) phenyl)-1H-1,2,4-triazol-3-yl)benzoic acid in high yield (85-95%) using inexpensive commercially available reagents. It would also be desirable if the by-products could be easily removed from the acyl azide.

SUMMARY OF THE INVENTION

The present invention provides such conditions. Thus, the present invention concerns a process for preparing certain triaryl acyl azides of the Formula (I),

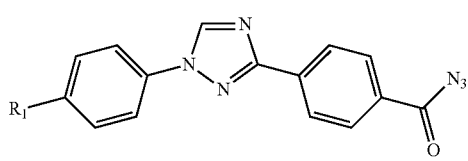

wherein
$R_1$ represents $(C_1-C_6)$ haloalkyl or $(C_1-C_6)$ haloalkoxy, which comprises
a) contacting a triaryl acid of Formula (II)

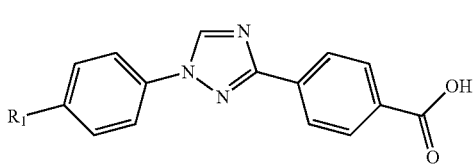

wherein
R₁ is as previously defined, with an inorganic acid halide halogenating agent in an organic solvent that is inert to the halogenating agent to provide a triaryl acid halide of Formula (III)

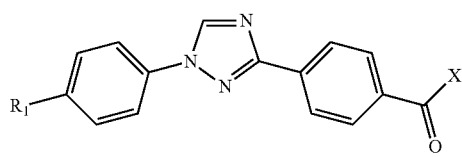

wherein
R₁ is as previously defined, and
X represents Cl or Br,
and
b) contacting the triaryl acid halide of Formula (III) with an aqueous solution of sodium azide in an organic solvent that is inert to sodium azide and the triaryl acid chloride.

Alternatively, the present invention concerns a process for preparing certain triaryl acyl azides of the Formula (I),

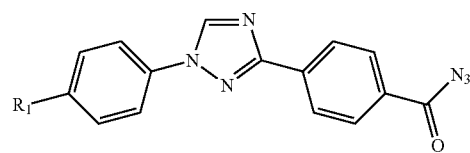

wherein
R₁ represents (C₁-C₆) haloalkyl or (C₁-C₆) haloalkoxy,
which comprises
a) contacting a triaryl acid of Formula (II)

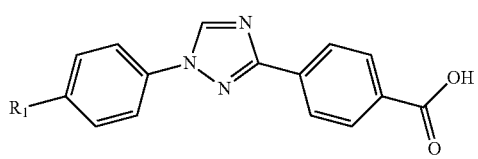

wherein
R₁ is as previously defined,
with chlorocarbonate of Formula (IV)

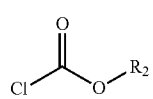

wherein
R₂ represents (C₁-C₆) alkyl, phenyl or benzyl,
in the presence of a base in an organic solvent that is inert to the chlorocarbonate to provide a triaryl mixed anhydride of Formula (V)

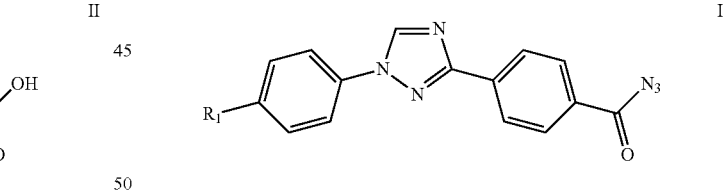

wherein
R₁ and R₂ are as previously defined,
and
b) contacting the triaryl mixed anhydride of Formula (V) with an aqueous solution of sodium azide in an organic solvent that is inert to sodium azide.

In another embodiment of the invention, R₁ represents $OCF_2CF_3$.

In another embodiment of the invention, R₂ represents $CH_2CH_3$, $C(CH_3)_3$ or $CH_2C_6H_5$.

DETAILED DESCRIPTION OF THE INVENTION

Throughout this document, all temperatures are given in degrees Celsius, and all percentages are weight percentages unless otherwise stated.

The term "alkyl", as well as derivative terms such as "haloalkyl" and "haloalkoxy", as used herein, include within their scope straight chain, branched chain and cyclic moieties. Thus, typical alkyl groups are methyl, ethyl, propyl, butyl, pentyl, hexyl, 1-methylethyl, 1,1-dimethylethyl, 1-methylpropyl, 2-methylpropyl, cyclopropyl, cyclobutyl, cyclopentyl and cyclohexyl. The terms "haloalkyl" and "haloalkoxy" includes alkyl or alkoxy groups substituted with from one to the maximum possible number of halogen atoms, all combinations of halogens included. Unless specifically defined otherwise, the term "halogen" or "halo" includes fluorine, chlorine, bromine and iodine, with fluorine being preferred.

The present invention concerns a process for preparing certain triaryl acyl azides of the Formula (I),

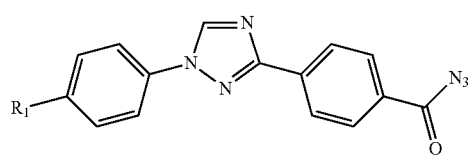

wherein
R₁ represents (C₁-C₆) haloalkyl or (C₁-C₆) haloalkoxy.
By either forming a triaryl acid halide of Formula (III)

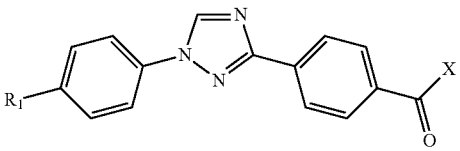

wherein
R₁ represents (C₁-C₆) haloalkyl or (C₁-C₆) haloalkoxy, and
X represents Cl or Br, or a triaryl mixed anhydride of Formula (V)

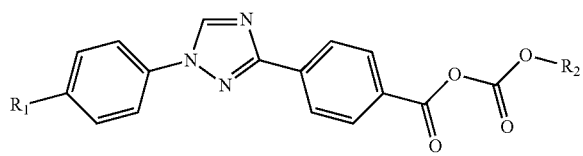

wherein

R₁ represents (C₁-C₆) haloalkyl or (C₁-C₆) haloalkoxy, and

R₂ represents C₁-C₆ alkyl, phenyl or benzyl and subsequently treating with aqueous sodium azide, triaryl acyl azides are prepared in high yield (85-95%) using inexpensive commercially available reagents in a process in which by-products are easily removed from the triaryl acyl azide.

The conversion of the triaryl acid II to the triaryl acid chloride III is conducted by treating the triaryl acid II with an inorganic acid halide halogenating agent in an organic solvent that is inert to the halogenating agent at a temperature from about 0° C. to about 60° C. The halogenating agent is an inorganic acid halide such as thionyl chloride or bromide, phosphorus trichloride or tribromide or phosphorus pentachloride or pentabromide. Thionyl chloride is preferred since the by-products are gases and the triaryl acid chloride is easily isolated. A stoichiometric excess of halogenating agent is usually used with about 2 to about 5 equivalents being preferred. The reaction is conducted in an organic solvent that is inert to the halogenating agent, such as chlorinated hydrocarbons like dichloromethane.

In a typical reaction, the triaryl acid II is suspended in a chlorinated hydrocarbon solvent and the inorganic acid halide halogenating agent is added. The mixture is heated at about 40° C. until the reaction is completed. Triaryl acid chloride III is isolated by removal of the solvent.

In the second step, the triaryl acid chloride III is reacted with an aqueous solution of sodium azide in an organic solvent that is inert to sodium azide and the triaryl acid chloride at a temperature from about 0° C. to about ambient. Approximately a 1:1 molar ratio of the triaryl acid chloride III and sodium azide may be used, however, a slight excess of sodium azide is preferred.

In the second step, triaryl acid chloride III is reacted with an aqueous solution of sodium azide in an organic solvent that is inert to sodium azide and the triaryl acid chloride. Preferably, the inert organic solvent should be miscible with water. Such inert water-miscible organic solvents include ethers like tetrahydrofuran or dimethoxyethane, nitriles like acetonitrile, ketones like acetone or methyl isobutyl ketone, and alcohols like methanol, ethanol, isopropanol or butanol. Alternatively, the inert organic solvent can be immiscible with water if a phase transfer catalyst is employed. Such inert water-immiscible organic solvents include hydrocarbons like toluene or xylene and chlorinated hydrocarbons like dichloromethane. A phase-transfer catalyst or PTC is a catalyst that facilitates the migration of a reactant from one phase into another phase where reaction occurs. Phase-transfer catalysts for anionic reactants like azide are often quaternary ammonium and phosphonium salts. Typical catalysts include tetraalkylammonium chlorides or bromides like benzyltrimethyl-ammonium chloride or tributylammonium bromide, tetraalkylammonium hydrogen sulfate like tributylammonium hydrogen sulfate, or tetraalkyl-phosphonium chlorides or bromides like hexadecyltributylphosphonium bromide.

In a typical reaction, the triaryl acid chloride III is suspended in an inert water-miscible organic solvent and cooled while an aqueous solution of sodium azide is added dropwise at a rate to maintain the temperature below about 5° C. The resulting suspension is stirred at about 0 to about 5° C. until the reaction is completed. The triaryl acyl azide can be isolated by filtration.

The conversion of the triaryl acid II to the triaryl mixed anhydride V is conducted by treating the triaryl acid II with a (C₁-C₆) alkyl, phenyl or benzyl chlorocarbonate in the presence of a base in an organic solvent that is inert to the chlorocarbonate at a temperature from about 0° C. to about 60° C. Approximately a 1:1 molar ratio of the triaryl acid II and chlorocarbonate may be used, however, a slight excess of chlorocarbonate is preferred.

Similarly, approximately a 1:1 molar ratio of base to chlorocarbonate is required as an acid acceptor. Suitable bases include alkali metal carbonates and amine bases. Tertiary amine bases like triethylamine and aromatic amine bases like pyridine are preferred.

Since it is most convenient to use the triaryl mixed anhydride V in the second step without isolation, the inert organic solvent is the same for both steps. Preferably, the inert organic solvent should be miscible with water. Such inert water-miscible organic solvents include ethers like tetrahydrofuran or dimethoxyethane, nitriles like acetonitrile, and ketones like acetone or methyl isobutyl ketone. Alternatively, the inert organic solvent can be immiscible with water if a phase transfer catalyst is employed. Such inert water-immiscible organic solvents include hydrocarbons like toluene or xylene and chlorinated hydrocarbons like dichloromethane.

In the second step, the triaryl mixed anhydride V is reacted with an aqueous solution of sodium azide in an inert organic solvent at a temperature from about 0° C. to about ambient. Approximately a 1:1 molar ratio of the triaryl mixed anhydride V and sodium azide may be used, however, a slight excess of sodium azide is preferred.

In the second step, triaryl mixed anhydride V is reacted with an aqueous solution of sodium azide in an inert organic solvent. Preferably, the inert organic solvent should be miscible with water. Such inert water-miscible organic solvents include ethers like tetrahydrofuran or dimethoxyethane, nitriles like acetonitrile, ketones like acetone or methyl isobutyl ketone, and alcohols like methanol, ethanol, isopropanol or butanol. Alternatively, the inert organic solvent can be immiscible with water if a phase transfer catalyst is employed. Such inert water-immiscible organic solvents include hydrocarbons like toluene or xylene and chlorinated hydrocarbons like dichloromethane. A phase-transfer catalyst or PTC is a catalyst that facilitates the migration of a reactant from one phase into another phase where reaction occurs. Phase-transfer catalysts for anionic reactants like azide are often quaternary ammonium and phosphonium salts. Typical catalysts include tetraalkylammonium chlorides or bromides like benzyltrimethylammonium chloride or tributylammonium bromide, tetraalkylammonium hydrogen sulfate like tributylammonium hydrogen sulfate, or tetraalkylphosphonium chlorides or bromides like hexadecyltributylphosphonium bromide.

In a typical reaction, the triaryl acid II is dissolved or suspended in the inert organic solvent. The mixture is cooled to about 10° C. and the base is added. The mixture is further cooled to about 0° C. and the chlorocarbonate is added at a rate to maintain the temperature at about 5° C. The mixture is stirred until the reaction is completed. The mixture is again cooled to about 0° C. and aqueous sodium azide is added at a rate to maintain the temperature at about 5° C. After completion of the reaction, the mixture is diluted with water and the solid product collected by filtration.

The following examples are presented to illustrate the invention.

EXAMPLES

Example 1: Preparation of 4-(1-(4-(perfluoroethoxy)phenyl)-1H-1,2,4-triazol-3-yl) benzoyl azide from mixed anhydride

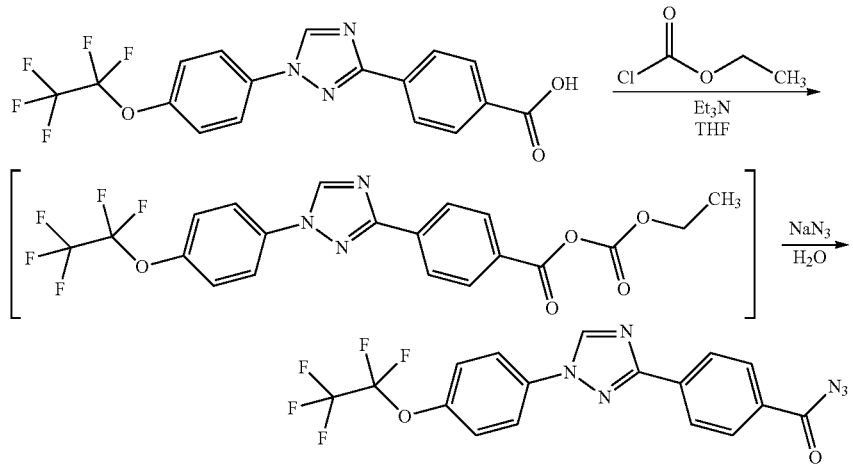

Into a 3-L, three-neck round bottom flask equipped with overhead stirrer, temperature probe, addition funnel, and nitrogen inlet, was added 4-(1-(4-(perfluoroethoxy)phenyl)-1H-1,2,4-triazol-3-yl) benzoic acid (100 g, 238 mmol) and tetrahydrofuran (550 mL). This gave a brown solution which was cooled to 9° C. and triethylamine (36.9 mL, 262 mmol) was added all at once. The temperature rose from 9° C. to 11° C. The solution was cooled back down to 1.4° C. and ethyl chloroformate (28.7 g, 25.3 mL, 262 mmol) was added drop wise over a 12 minute period. The mixture exothermed from 1.4° C. to 5.5° C., with the average addition temperature being 4.4° C. The mixture was allowed to stir for 30 minutes and assayed by LCMS (reaction complete). To the reaction mixture, at 0.3° C., was slowly added a solution of sodium azide (17.01 g, 262 mmol) in water (300 mL). The azide solution was added at such a rate as to keep the temperature below 4° C. After addition was complete, the mixture was allowed to stir at 0° C. for 2 hours. The ice bath was removed and a sample was pulled while still cold (5° C.) and assayed by LCMS and $^1$H NMR (reaction complete). The reaction was allowed to stir for 16 hours at 25° C. The reaction was cooled to 5.5° C., water was slowly added (1100 mL) over 20 minutes. The mixture exothermed from 5.5° C. to 11.5° C. and was stirred at <10° C. for 1 hour. The solids were collected by vacuum filtration, washed with water (3×500 mL), and vacuum dried under a stream of nitrogen to constant weight providing the title compound as a white solid (95.3 g, 90%): $^1$H NMR (400 MHz, CDCl$_3$) δ 8.61 (s, 1H), 8.35-8.23 (m, 2H), 8.19-8.07 (m, 2H), 7.82 (d, J=9.0 Hz, 2H), 7.42 (d, J=8.9 Hz, 2H); EIMS m/z 425 (|M$^+$|).

Example 2: Preparation of 4-(1-(4-(perfluoroethoxy)phenyl)-1H-1,2,4-triazol-3-yl)benzoyl chloride

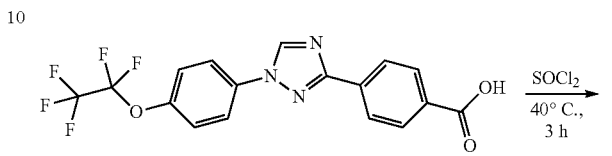

-continued

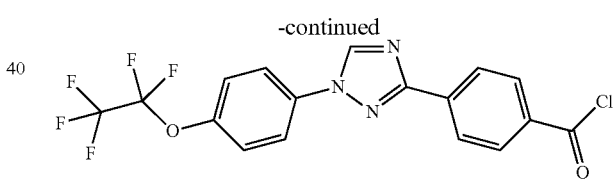

Into a 250 mL three-necked round bottom flask fitted with an overhead stirrer, nitrogen inlet, T-type J-Kem thermocouple, and reflux condenser was added 4-(1-(4-(perfluoroethoxy) phenyl)-1H-1,2,4-triazol-3-yl)benzoic acid (4.1 g, 10 mmol). To the solid was added dichloromethane (30 mL). This gave a white suspension. To the suspension was added thionyl chloride (5.8 g, 49 mmol). This gave a white suspension and the mixture exothermed slightly from 19° C. to 22° C. over 5 minutes. The mixture was heated to 40° C. with a heating mantle for 3 hours then allowed to cool to 23° C. for 16 hours. This gave an off-white suspension. The mixture was transferred to a 500 mL rotary evaporation flask and rotary evaporated (24-95° C., 50 mmHg, 1 hour) providing the title compound as a tan solid (4.7 g, 108% mass balance). The solid is soluble in tetrahydrofuran and dimethylformamide and partially soluble in acetone: $^1$H NMR (400 MHz, CDCl$_3$) δ 9.90 (s, 1H), 8.48 (d, J=8.2 Hz, 1H), 8.43-8.18 (m, 2H), 8.04 (d, J=8.8 Hz, 2H), 7.48 (d, J=8.7 Hz, 1H); Anal. Calcd for C$_{17}$H$_9$ClF$_5$N$_3$O$_2$: C, 48.88; H, 2.17; N, 10.16; Cl, 8.49; F, 22.74. Found: C, 45.49; H, 2.41; N, 9.27; Cl, 11.19; F, 20.41.

Example 3: Preparation of 4-(1-(4-(perfluoroethoxy)phenyl)-1H-1,2,4-triazol-3-yl) benzoyl azide from Acid Chloride

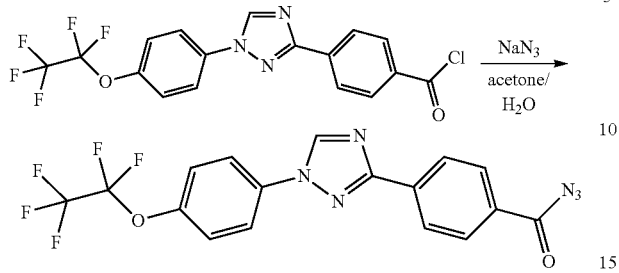

Into a 250 mL three-necked round bottom flask fitted with an overhead stirrer, nitrogen inlet, T-type J-Kem thermocouple, and addition funnel was added 4-(1-(4-(perfluoroethoxy) phenyl)-1H-1,2,4-triazol-3-yl)benzoyl chloride (4.0 g, 10 mmol). To the solid was added acetone (50 mL). This gave a tan suspension. The tan suspension was cooled to 2° C. in an ice bath and an aqueous solution of sodium azide (0.75 g, 11 mmol) in water (10 mL) was added drop wise (caution: exotherm) over 15 minutes being careful to keep the internal temperature below 6° C. During the addition, the reaction exothermed from 2° C. to 6° C. This gave a white thick suspension. The suspension was stirred at 2° C. for 2 hours. Analysis by LCMS indicated the reaction was done. The reaction was diluted with water (100 mL) and stirred at 5° C. for 1 hour. The solids were collected by vacuum filtration and rinsed with water (2×25 mL). This gave an off-white wet cake (5.9 g). The wet cake was allowed to air dry at ambient temperature for 20 hours until constant mass was achieved providing the title compound as an off-white solid (3.7 g, 90%). The solid was analyzed by $^1$H-NMR, $^{19}$F-NMR, and LCMS and matched authentic material. The $^1$H-NMR showed about 86% desired acyl azide with 14% acid

Example 4: Preparation of 4-(1-(4-(perfluoroethoxy)phenyl)-1H-1,2,4-triazol-3-yl)benzoyl azide via PTC Reaction in Toluene Into a 250 mL three-necked round bottom flask fitted with an overhead stirrer, nitrogen inlet, T-type J-Kem thermocouple, and addition funnel was added 4-(1-(4-(perfluoroethoxy) phenyl)-1H-1,2,4-triazol-3-yl)benzoic acid (5.0 g, 12 mmol). To the solid was added toluene (50 mL). This gave a light pink suspension. To the suspension was added neat triethylamine (1.4 g, 14 mmol) in one portion. The reaction immediately turned to a dark pink solution and exothermed from 25° C. to 28° C. Then over 3 minutes it turned back into a light pink suspension. To the suspension was added ethyl chloroformate (1.5 g, 14 mmol) in one portion. The reaction turned to a dark pink solution slowly over 5 minutes and exothermed from 25° C. to 30° C. Then slowly over 5 minutes the reaction tuned back into a pink suspension. The reaction was stirred at 25° C. for 30 minutes. Analysis by LCMS showed the reaction to be complete giving the mixed anhydride. The pink suspension was filtered to remove the white solids and the solids were rinsed with toluene (50 mL). The rinses were added to the filtrate and the resulting filtrate (dark pink solution) was place into an addition funnel and added drop wise at a rate of 6 mL/minute to a mechanically stirred 2% (w/w) solution of sodium azide (0.90 g, 14 mmol) in water containing tetrabutylammonium hydrogen sulfate (0.040 g, 0.13 mmol). The reaction exothermed very slowly from 21.1° C. to 21.8° C. during the addition. The reaction was stirred for 1 hour and analysis by LCMS showed the reaction to be complete with formation of the acyl azide.

What is claimed is:

1. A process for preparing triaryl acyl azides of the Formula (I),

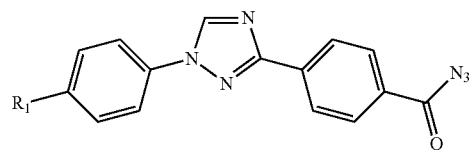

wherein
R$_1$ represents (C$_1$-C$_6$) haloalkyl or (C$_1$-C$_6$) haloalkoxy,
which comprises
a) contacting a triaryl acid of Formula (II)

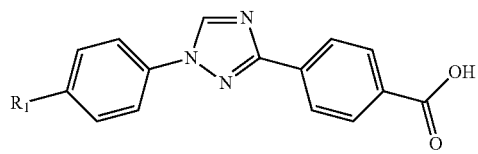

wherein
R$_1$ is as previously defined,
with chlorocarbonate of Formula (IV)

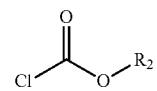

wherein
R$_2$ represents (C$_1$-C$_6$) alkyl, phenyl or benzyl,
in the presence of a base in an organic solvent that is tetrahydrofuran or dimethoxyethane to provide a triaryl mixed anhydride of Formula (V)

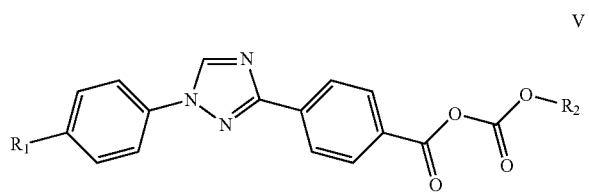

wherein
R$_1$ and R$_2$ are as previously defined, and
b) contacting the triaryl mixed anhydride of Formula (V) with an aqueous solution of sodium azide in the organic solvent tetrahydrofuran or dimethoxyethane.

2. The process of claim 1 in which R$_1$ is OCF$_2$CF$_3$.

3. The process of claim 1 in which R$_2$ is CH$_2$CH$_3$.

4. The process of claim 1 in which the base is an alkali metal carbonate, a tertiary amine or an aromatic amine.

* * * * *